United States Patent [19]
Kessler et al.

[11] Patent Number: 5,639,481
[45] Date of Patent: Jun. 17, 1997

[54] METHOD FOR THE THERAPEUTIC TREATMENT OF A MAMMALIAN EYE USING AN ADMIXED COMPOSITION CONTAINING FREE MOLECULAR IODINE

[75] Inventors: Jack H. Kessler, Southborough; James C. Richards, Framingham, both of Mass.

[73] Assignee: Symbollon Corporation, Sudbury, Mass.

[21] Appl. No.: 551,478

[22] Filed: Nov. 1, 1995

Related U.S. Application Data

[63] Continuation-in-part of Ser. No. 324,391, Oct. 17, 1994, abandoned.

[51] Int. Cl.$^6$ .................. A01N 59/22; C12N 9/96
[52] U.S. Cl. .................. 424/667; 435/188; 514/5
[58] Field of Search ................. 514/5; 424/667; 435/188

[56] References Cited

U.S. PATENT DOCUMENTS

| | | | |
|---|---|---|---|
| 3,028,300 | 4/1962 | Cantor et al. | 167/17 |
| 4,227,161 | 10/1980 | Kessler | 424/94.4 |
| 4,271,149 | 6/1981 | Wincov et al. | 424/150 |
| 4,370,199 | 1/1983 | Orndoff | 162/161 |
| 4,576,817 | 3/1986 | Montgomery | 424/94 |
| 4,937,072 | 6/1990 | Kessler et al. | 424/94.4 |
| 4,996,146 | 2/1991 | Kessler | 435/28 |
| 5,169,455 | 12/1992 | Kessler | 134/42 |
| 5,185,371 | 2/1993 | Rubinstein | 422/28 |

OTHER PUBLICATIONS

Transfusion 1994 34: 322–327 entitled: Inactivation of lipid etc F.A. Highsmith Journal of Infectious Diseases vol. 167 p. 1027 1993.
Nunez & Pommier European Journal of Biochemistry vol. 7, pp. 286–293.
Morrison & Schonbaum Annual Review of Biochemistry vol. 45 pp.851–888.
Ohtaki et al. Journal of Biochemistry vol. 256 pp. 805–810 1981.

*Primary Examiner*—John W. Rollins
*Assistant Examiner*—Deborah K. Ware

[57] ABSTRACT

The present invention relates generally to an enzymatically generated iodine microbicide and more specifically to the use of such a microbicide for the inactivation of pathogenic organisms that are contaminants in or on sensitive biological materials such as the human eye or tissue culture cells. The biocidal agent from the enzymatic reaction is free molecular iodine generated so as to establish a minimum level of 5 ppm in a fashion such that free molecular iodine comprises at least 25% of the total iodine species present on a molar basis.

3 Claims, No Drawings

METHOD FOR THE THERAPEUTIC TREATMENT OF A MAMMALIAN EYE USING AN ADMIXED COMPOSITION CONTAINING FREE MOLECULAR IODINE

The present invention is a continuation-in-part of application Ser. No. 08/324,391, filed Oct. 17, 1994, now abandoned.

FIELD OF THE INVENTION

The present invention relates generally to the enzymatic formation of an iodine-based microbicide. The biocidal agent from the enzymatic reaction is free molecular iodine that is generated in situ by the reaction of peroxidase, iodide and hydrogen peroxide. The germicides contemplated under this application ultilizes free molecular iodine that is enzymatically generated to inactive pathogenic organisms that are contaminants in and on sensitive biological materials. A wide range of sensitive biological materials are contemplated under this application. These materials include cell lines used for tissue culture, red blood cells, blood plasma, blood proteins, human cells such as sperm, human tissues such as skin, and human organs such as the eye. It is preferred for a liquid microbicide to inactivate all unwanted pathogens and not substantially reduce the biological activity of the sensitive biological material of interest. Inactivation of pathogens associated with biological materials is difficult to accomplish since there is a conflict between biocidal activity and toxicity with sensitive living cells such as those that comprise the human eye.

DESCRIPTION OF THE RELATED ART

Sensitive biological products from human and animal sources are widely used for therapeutic, diagnostic and experimental purposes. Such products are subject to contamination by virtue of their natural environment that presents favorable conditions for microbial contamination. Frequent contaminants include bacteria, viruses and fungi. Diagnostic tests for the presence of such pathogens are available but there is no way to insure that these products are free from unwanted contaminants. A good example of this is the transfusion of human blood products that currently carries a well-known risk of transmitting a number of viruses and bacteria.

A large variety of chemical germicides have been used in the medical profession and biomedical industry to inactivate unwanted bacteria, viruses and fungi. The majority of these chemical germicides are either toxic or destructive to organic material and, as a result, these disinfectants are not suitable for use with sensitive biological materials. U.S. Pat. No. 5,185,371 describes a method to disinfect blood products that relies upon diluting a germicide in one of the following compositions: 0.9% aqueous sodium chloride, 5% aqueous dextrose, sugar solutions or other diluents that ameliorate the chemical incompatibilities of the liquid germicides with blood and blood products.

F. A. Highsmith et al. (*Journal of Infectious Diseases*, volume 167, page 1027,1993) describe methods that utilize a chemically modified polyvinylpyrrolidone-iodine complex. The compositions and methods described in Highsmith have been used to disinfect blood products. The compositions of Highsmith contain a large number of iodine species including free molecular iodine. The intuitive appeal of using iodine for such applications is obvious since iodine is a nutritional additive.

All of the prior art related to decontamination of sensitive biological materials with iodine utilize iodophors. Iodophors are compositions that utilize povidone-iodine or other complexesions that contain iodine bound to a high molecular weight polymer. The use of an iodophor increases the absolute concentration of iodine species that are required to inactivate pathogens as compared to a composition of free molecular iodine that does not contain high molecular weight polymers which bind iodine. Iodophors are not the preferred form of iodine for disinfection of sensitive biological material since all forms of iodine can be toxic. In this regard the prior art does not directly address the critical parameters required to effectively utilize iodine for the disinfection of biological materials. Free molecular iodine is the biocidal species of iodine and therefore the key to effective use of iodine with sensitive biological materials in accordance with the present invention is to be able to control the level of free molecular iodine such that free molecular iodine is the principal iodine species relative to the other species of iodine. In addition, it is highly preferred to substantially maintain the level of free molecular iodine under the conditions of pH and ionic strength that are not destructive or irritating to the biological materials.

Iodophors have been used to disinfect the human eye however the ratio of free molecular iodine to other iodine species is less than 1/100. This application describes compositions that can form a non-irritating microbicide possessing a plurality of iodine species having at least 25% free molecular iodine on a molar basis with the free molecular iodine concentration between 5 and 125 ppm formed by enzymatically reacting peroxidase, iodide and hydrogen peroxide in an aqueous medium in a molar ratio of hydrogen peroxide to iodide of no greater than four and a maximum concentration level of hydrogen peroxide of 0.015% before applying the microbicide to the human eye.

In order for free molecular iodine to be effective, the level of this biocidal agent must be substantially maintained for a period of time that is sufficient to inactivate all of the unwanted pathogens. However, the chemical activity of free molecular iodine must not also be controlled in order to substantially maintain the integrity of the biological material of interest. Because of the conflicting attributes of biocidal activity and biological compatibility, it is important to eliminate or minimize other iodine species present which will contribute toxicity and chemical incompatibilities but do not necessarily contribute biocidal efficacy. In addition, the concentration of other non-biocidal cytotoxic chemicals should be minimized since they serve as a potential source of contamination and incompatibility.

The pH that is most compatible with the overwhelming majority of biological materials contemplated under this application is pH 6.8 to 7.1. While it is not necessary to decontaminate the biological materials of interest at a pH of 7.0 it is highly preferred to maintain a pH that is as close to 7.0 as possible in order to minimize the potential for damage. A neutral pH introduces an additional factor that complicates the use of free molecular iodine in disinfection. Free molecular iodine is not stable at a neutral pH and, as a result, the duration of treatment is a critical parameter.

One of the disinfectants identified in U.S. Pat. No. 5,185, 371 is 10% povidone-iodine which is frequently represented as PVP-$I_2$. PVP-$I_2$ is a complex of iodine with povidone. It contains not less than 9.0% by weight, and not more than 12% by weight of thiosulfate titratable iodine. In addition, PVP-$I_2$ typically contains not more than 6.6% by weight of iodide ions. Additionally, iodate and other inorganic species are typically added to PVP-$I_2$. PVP-$I_2$ is available commercially from many different manufacturers and the pH of these products will vary by manufacturer. However, PVP-$I_2$ is strongly buffered at acidic conditions that typically range between pH 3.5 and 4.5.

The distribution of iodine species in PVP-$I_2$ does not favor its use for sensitive biological materials. PVP-$I_2$ is not a preferred degerming agent for biological materials since less than 0.2% of the iodine contained in such compositions is in the form of free molecular iodine. In addition, the pH of these compositions are toxic to most of the cells and tissues contemplated under this application. PVP-$I_2$ was designed to be applied directly to intact skin. The epidermis of mammalians consists of dead cells that are significantly less sensitive to harsh chemicals than living cells.

U.S. Pat. No. 5,185,371 describes the treatment of blood and blood products with PVP-$I_2$ at concentrations that range from 0.01% to 0.5% by weight for up to 5 minutes. This application prescribes a concentration range for PVP-$I_2$ that corresponds to a 1/200 to a 1/10,000 dilution of PVP-$I_2$. When PVP-$I_2$ is diluted in normal saline at 1/200 the pH of the resulting solution is ≈4.6 and the level of free molecular iodine is ≈10 ppm. When PVP-$I_2$ is diluted in normal saline at 1/10,000 the pH of the resulting solution is ≈5.4 and the level of free molecular iodine is ≈0–0.5 ppm. The combination of free molecular iodine, pH and contact time described in U.S. Pat. No. 5,185,371 is not adequate to effectively inactivate most of the bacteria and viruses of interest in the presence of a competing bioburden. It is known that a significant amount of iodine and/or extended contact times are required to completely inactivate non-lipid-enveloped (Highsmith F. A. et al., *Transfusion*, volume 34, page 322, 1994).

Accordingly, there presently is a need to provide an iodine based method to disinfect sensitive biological materials including cell culture, human blood products, animal blood products and human and animal tissue products. Iodine based compositions have been formulated to disinfect sensitive biological materials but these compositions have several drawbacks. Iodine is an effective biocide and unlike other biocides, iodine is required for proper human nutrition and thyroid function. The difficulty with previous iodine based compositions is that they have unfavorable characteristics of pH and ionic strength and that active biocidal iodine (i.e., free molecular iodine) is (a) combined with other chemical species that are not biocidal and (b) not the predominant iodine species.

SUMMARY OF THE DISCLOSURE

The objectives of the present invention are accomplished by generating an iodine based disinfectant under conditions such that the free molecular iodine so generated is in a concentration range of betweeen 5 and 330 ppm. Such an iodine composition can be formed in an aqueous environment that is maximally compatible with a given biological material. Surprisingly such a solution will not only disinfect biological products but will do so without damage to the material of interest such as blood cells and tissue cells. Such compositions may be used for therapeutic or diagnostic purposes following the disinfectant procedure. It is presently believed that the disinfectant compositions of the present invention will render sensitive biological materials like tissue culture cells or a human eye safe, i.e., inactivate harmful bacteria, viruses and virus-like agents that may be present.

Iodine based germicides are well known in the art. The method used to generate the iodine based germicide of this application is to use peroxidase in combination with iodide and hydrogen peroxide. It is known from Kessler (U.S. Pat. No. 4,227,161, U.S. Pat. No. 5,169,455, U.S. Pat. No. 4,996,146 and U.S. Pat. No. 4,937,072), Orndoff (U.S. Pat. No. 4,370,199) and Montgomery (U.S. Pat. No. 4,576,817) that a combination of peroxidase, peroxide and iodide anions will form a bactericide in an aqueous environment. The bactericidal efficacy of this combination results from the enzymatic reaction that occurs when peroxidase, hydrogen peroxide and iodide react in solution. Peroxidase is known to effect the transfer of electrons from iodide to hydrogen peroxide. Hydrogen peroxide is converted into water by this reaction. Several possible reaction products have been postulated for the iodide anion including: 1) iodine free radicals (Nunez and Pommier, *European Journal of Biochemistry*, volume 7, pages 286–293, 1969); 2) hypoiodite ion (Morrison and Schonbaum, *Annual Review of Biochemistry*, volume 45, pages 861–888, 1976); and 3) iodinium ion (Ohtaki, Nakagawa, Kimura and Yamakazi, *Journal of Biochemistry*, volume 256, pages 805–810, 1981).

It has been observed that under certain conditions these reactions will generate significant levels of free molecular iodine wherein said free molecular iodine comprises a significant percentage of all of the iodine species present. The phrase "free molecular iodine" is a term of art that refers to elemental iodine, the chemical species that is represented as $I_2$ and that is capable of being titrated with sodium thiosulfate. It has been observed that it is possible to generate defined levels of free molecular iodine across a wide pH range using compositions comprised of peroxidase, peroxide and iodide. The exact level of available iodine in these compositions is a function of the concentration levels of peroxide, iodide, peroxidase, buffering agents, pH and other additives.

It is understood that if materials like red blood cells or an eye are to be disinfected, the disinfectant composition must be substantially isotonic in order to minimize toxicity. The disinfectant concentration and the time required to effectively inactivate any pathogenic organisms are dependent upon the level of free molecular iodine in the final environment. Suitable concentrations of free molecular iodine are a function of the precise biological material of interest. In general the range of free molecular iodine that is suitable ranges from 5 to 330 ppm. The amount of time that is required to inactivate the pathogenic organisms of interest is a direct function of the level of free molecular iodine, the pathogens of interest and the level of biological material in the composition.

In order to practice this invention to disinfect the eye of mammals there are several important considerations. It is highly preferred to make the composition isotonic to human lachrymal fluid. Alternately, one can control the ionic strength of the composition such that it lies between 280 and 300 milliosmols. It is well understood by one skilled in the art that this can be accomplished by adding agents such as sodium chloride to the composition. Polymers such as hydroxyethyl cellulose, methylcellulose and polyvinylalcohol are frequently used in ocular compositions as are many other polymers that are familiar to one skilled in the art. These materials are suitable for the compositions disclosed in this application provided that they are combined in a fashion that does not substantially increase the overall concentration of iodine necessary to achieve the desired biocidal activity. The ocular compositions contemplated under this application include conditions caused by viruses, bacteria, fungi and acanthameba.

The free molecular iodine is allowed to dissipate via hydrolysis in the composition after the free molecular iodine contacts the sensitive biological material of interest. Alternatively the iodine in the composition can be separated by a plurality of means that are familiar to one skilled in the art including adding materials, like cyclodextrin, that bind iodine or passing the composition through columns that contain iodine binding materials.

DETAILED DESCRIPTION OF THE INVENTION

A method is provided in which most types of pathogenic organisms are completely inactivated in the presence of sensitive biological materials. Additionally, the biological materials may be used subsequently for therapeutic or diagnostic purposes. The invention is based upon the unexpected discovery that elevated concentrations of free molecular iodine are compatible with many sensitive biological materials including, but not limited to, red blood cells, blood proteins, animal tissues and organs including eyes.

In accordance with this invention free molecular iodine is generated in situ and contacted with the biological material of interest. The level of free molecular iodine that is required to be in contact with the contaminated material is between 5 and 330 ppm which corresponds to an input level of iodide anion that is between 25 ppm and 1660 ppm.

The pH of the aqueous environment must be controlled to be between pH 5.0 and 7.1. The preferred pH range in which to treat the biological material of interest is between pH 6.0 and 7.0. The contact time for the free molecular iodine can be varied widely and will depend upon the level of organic material in the composition and the temperature at which the material is treated. The contact time and temperature of treatment must be derived empirically for each application.

Free molecular iodine is introduced by using peroxidase, iodide, and a source of hydrogen peroxide. It is obvious that the concentration of free molecular iodine used must be adequate to inactivate the contaminating pathogens; however, what is less obvious and equally critical is to generate an iodine based germicide whose principal component is free molecular iodine. By contacting the material of interest with an iodine composition that is principally comprised of free molecular iodine one minimizes the potential for chemical incompatibilities and chemical contamination. Free molecular iodine should comprise at least 25% on a molar basis of all of the iodine species present after the iodine based germicide has been placed in an aqueous environment with the biological material of interest.

The reactants that comprise the peroxidase catalyzed oxidation of iodide must be controlled to yield a suitable result. The reaction should be established so as to efficiently convert iodide ions into free molecular iodine. Additionally, it is preferable to establish reaction conditions that convert at least 50% of the the initial concentration of hydrogen peroxide into water and the concentration of hydrogen peroxide that is left in contact with the biological material of interest after initiation of the enzymatic reaction should not be above a level of 0.015%. In order to optimally convert iodide into free molecular iodine the molar ratio of hydrogen peroxide to iodide should be initially established in a 1/2 molar proportion. It is highly preferred to limit this ratio to no greater than 4.

The preferred oxidant of this invention is hydrogen peroxide. Any material that acts as a source of hydrogen peroxide when admixed in an aqueous environment is suitable for the present invention. The term "source of peroxide" for purposes of the present invention and as used herein shall mean any material alone or in combination which can serve as precursors for hydrogen peroxide including metal peroxides, percarbonates, persulphates, perphosphates, peroxyesters, urea peroxide, peroxyacids, alkylperoxides, acylperoxides and perborates. Alternately methyl peroxide can also be used as a source of hydrogen peroxide. Mixtures of two or more of these substances can also be used. The preferred concentration for hydrogen peroxide is between 0.001 and 0.01% in the final composition prior to initiation of the oxidation of iodide.

The donor molecule of this invention is iodide anion. Suitable dry sources of iodide anion for this invention include sodium iodide and potassium iodide as well as other salts of iodide. Any compound which yields iodide anion upon dissolution in an aqueous environment is suitable for this application. The simple salts of iodide are preferred and have the advantage of being less costly. Additionally, they have a long shelf life in solid form.

Iodide anion can be provided to the system in a liquid form if it is kept stable prior to use. Specifically, it is preferred not to contact the iodide anion with hydrogen peroxide. The concentration iodide that will yield a suitable level of iodine varies with the pH of the contemplated formulation. In addition, the required iodide level will vary dramatically depending upon the ratio of peroxide to iodide. When the preferred ratio of hydrogen peroxide to iodide of 1/2 is used, the preferred range for iodide anions is between 0.0015 and 0.10 grams per liter in the final reconstituted formulation prior to initiation of the enzymatic reaction. However, for some contemplated applications it is possible to less efficiently convert iodide into free molecular iodine and therefore the potentially useful range is for iodide anion is between 0.05 and 0.30 grams per liter in the final reconstituted formulation prior to initiation of the enzymatic reaction. These ranges of iodide anion in conjunction with pH and the concentration of the other additives are anticipated to yield a concentration of free molecular iodine within a range of 5 to 330 ppm.

The peroxidase enzyme of this invention is identified by the International Union of Biochemistry and the International Union of Pure and Applied Chemistry by the Enzyme Commission identification No. E.C. 1.11.1.7. This class of peroxidase can be obtained from a wide variety of sources including milk (lactoperoxidase), soy bean, and human leukocytes (myerloperoxidase). The least expensive peroxidase suitable for this application is horseradish peroxidase. It is anticipated that peroxidase that has been cloned from either horseradish, milk or human leukocytes will be suitable as a source of peroxidase for this application. Additionally, it has been observed that chemically modified peroxidase is suitable for use in this application. Modifications to the amino, carboxyl or carbohydrate moieties yield a suitable catalytic agent for inclusion in this application. The chemical modifications to peroxidase include cross-linking of enzyme molecules to each other, to solid surfaces or to other proteins. The chemical agents used for crosslinking include glutaraldehyde, maleimides, succinimides, carbodiimides, dicarboxylates, activated glycols, imidoesters, photoreactive azides and other agents known to one skilled in the art.

The aforementioned forms of peroxidase can be provided in a dry form such as the lyophilized peroxidase offered commercially or in a largely aqueous environment. If the peroxidase is supplied in an aqueous environment it typically will be incorporated into a medium that provides increased stability such as glycerol, dextrans, or other polyols or sugars in a suitable buffering medium that optimally contains calcium. The peroxidase of this application can be combined with many additives whether it is supplied dry or in an aqueous environment. The concentration range that peroxidase can be used over is between 0.00005 and 0.005 mg/mL in the final composition. The preferred range is between 0.0005 and 0.01 mg/mL in the final composition.

Suitable buffering agents for inclusion in the compositions contemplated in this application include water and hydroalcoholic mixtures buffered with glycine-glycine.HCl, potassium hydrogen phthalate-phthalic acid, citric acid-$Na_2HPO_4$, citric acid-$KH_2PO_4$—$H_3BO_3$-diethylbarbituric acid-NaOH, citric acid-sodium citrate, dimethylglutaric acid-sodium dimethylglutarate, acetic acid-sodium acetate, succinic acid-sodium succinate, potassium hydrogen phthalate-dipotassium phthalate, sodium cacodylate-cacodylic acid, sodium hydrogen maleate-disodium maleate, $Na_2HPO_4$—$NaH_2PO_4$, sodium bicarbonate-5% $CO_2$, imidazole-imidazole.HCl, boric acid-sodium borate, and the following buffers known to one skilled in the art as Good buffers Tris, MES, BIS-TRIS, ADA, ACES and PIPES.

If the biological material of interest is a mammalian cell then after the free molecular iodine composition and cells are mixed sufficiently to inactivate any pathogens that may be present, the iodine composition can be separated from the cells. The separation preferentially involves washing the cells in an automated cell washer or semi-automated cell washer with an isotonic solution until the disinfectant is substantially removed. Alternately, one can concentrate cells using a simple benchtop centrifuge, decant the supernatant that substantially contains the iodine germicide, and resuspend the cells in a medium of choice.

If the biological material of interest is a mammalian eye then the iodine composition can be rinsed from the eye after the contact. However, one advantage of the compositions described herein is that it is not neccessary to rinse since the concentration level of free molecular iodine is controlled relative to all other iodine species. In addition, the maximum iodine level and that the level of hydrogen peroxide is also controlled thereby forming a non-irritating therapeutic. The non-irritating microbicides described in this application have at least 25% free molecular iodine on a molar basis with the free molecular iodine concentration between 5 and 125 ppm formed by enzymatically reacting peroxidase, iodide and peroxide in an aqueous medium in a molar ratio of hydrogen peroxide to iodide of no greater than four and a maximum concentration level of hydrogen peroxide of 0.015% before applying the microbicide to the human eye. The preferred pH for an ophthalmic mendicament is between 5.5 and 7.1 althoug there are existing ophthalmic mendicatments with a pH that range from 3.5 to 8.5.

In a case where the sensitive biological materials consist of proteins, the iodine based germicide may be separated by precipitating out the plasma proteins in a generally conventional fashion or by passing the entire composition through a chromatographic separation medium which are very well known to one skilled in the art or by dialysis.

All of the foregoing operational principles and advantages of the present invention will be more fully appreciated upon consideration of the following detailed examples.

EXAMPLE 1

Iodine based compositions were prepared consisting principally of free molecular iodine. These compositions were prepared by incubating horseradish peroxidase, sodium iodide and hydrogen peroxide at a pH of 5.5, allowing these materials to incubate for a defined time period and then performing an analytical characterization of the resulting formulation.

The concentration of the following three iodine species were measured: free molecular iodine, triiodide and iodide anion. Free molecular iodine was measured potentiometrically by the method of Gottardi (Gottardi W., *Fresenius Z. Anal. Chem.*, volume 314, page 582, 1983). Two Corning model 345 pH meters were used to make the potentiometric measurements. The Corning electrodes that were used included a standard platinum electrode, a reference electrode and an iodide ion selective electrode. Triiodide was determined by performing a sodium thiosulfate titration to determine the level of total iodine and then subtracting the level of free molecular iodine from the total iodine level. The iodide ion concentration was determined directly by using a Corning iodide ion selective electrode.

There were three conditions explored using a citrate buffer at a pH of 5.5. All conditions used a final concentration of 5 ug/mL of horseradish peroxidase. The first condition (Treatment No. 1) used a concentration of sodium iodide that was 60 mg per liter and an equal molarity of hydrogen peroxide that was established using sodium percarbonate (0.025 grams per liter) as the source of hydrogen peroxide. Conditions two and three (Treatment Nos. 2 & 3) used 200 and 450 mg per liter of sodium iodide and 0.0833 and 0.187 grams per liter of sodium percarbonate respectively. The solutions were allowed to incubate for 60 minutes and the analytical measurements were made. The results are shown below in Table I.

TABLE I

| ppm of the Principal Iodine Species Sixty Minutes After Initiation of the Enzymatic Reaction | | |
|---|---|---|
| $I_2$-Iodine ppm | $I^-_3$-Triiodide ppm | $I^-$-Iodide ppm |
| Treatment 1 | | |
| 46.6 | <2 | 0.126 |
| Treatment 2 | | |
| 128 | <2 | 0.476 |
| Treatment 3 | | |
| 290 | 324 | 0.650 |

The conclusion we draw from the data shown in Table 1 is that it is possible to generate peroxidase based iodine germicides that are principally comprised of free molecular iodine. The data in Table shows the concentration of the three predominant iodine species: free moleuclar iodine, iodide anion and triiodide. The concentration of hypoiodous acid and iodate under the conditions used are insignificant as compared to the concentration of the three iodine species listed in Table I.

EXAMPLE 2

Iodine based compositions were prepared at a pH of 7.0 that consisted principally of free molecular iodine. These compositions were prepared by incubating horseradish peroxidase, sodium iodide and hydrogen peroxide at a pH of 7.0. These components were allowed to incubate for a defined time period and then analytical determinations were performed on the resulting composition. The weights and volumes of the chemical components used were: 0.2 grams of anhydrous citric acid, 450 mg of sodium iodide, 1.3 mL of 3% hydrogen peroxide, 100 mg of sodium bicarbonate and 3 mg of horseradish peroxidase. The composition was allowed to incubate for 15 minutes prior to performing the analytical determinations described in experiment 1. The results are shown below:

| ppm of Iodine Species | | |
|---|---|---|
| $I_2$-Iodine | $I_3^-$-Triiodide | $I^-$-Iodide |
| 178 | 72 | 0.82 |

The conclusion we draw is that it is possible to generate iodine based germicides at a pH of 7.0 that are principally comprised of free molecular iodine.

EXAMPLE 3

The three formulations described in experiment 1 were tested to determine their ability to inactivatge *Staphylococcus aureus* in the presence of $10^6$ red blood cells (RBC) per mL. The effect that these formulations had on the cellular morphology of the RBCs was determined by microscopic examination. A control experiment was performed using 10% PVP-$I_2$ at four dilutions that ranged from 1/20 to 1/10,000.

Whole blood was processed by the Ficoll lymphocyte isolation procedure. The red blood cells (RBC) were recovered and washed once with phosphate buffered saline and held at a concentration of $3.5 \times 10^9$ RBC/mL in Alsevers solution at 5° C.

Agar plates were inoculated by washing the growth from *Staphylococcus aureus* slants with 5 mL of 0.25 molar phosphate buffer dilution water at a pH of 7.0 (PBDW) into 100 mL of PBDW. One mL of this suspension was added to each of 7 nutrient agar plates which were incubated for 18–24 hr at 35°–37°. Bacterial colonies were removed from the agar surface using 1 mL of PBDW and a sterile swab. The suspension was standardized to give about $10^9$ cfu/mL using a Milton-Roy Spec 20 spectrophotometer.

One hundred mL of each test germicide were equilibrated to 25° C. in a water bath. Two minutes prior to the start of the assay, RBCs were added at a level of $10^6$ RBCs/mL. *S. aureus* was added to a level of $2.0 \times 10^8$ cfu/mL. One mL samples were removed after 30, 60, 120, and 300 second exposures and neutralized in 10 mLs 0.5% thiosulfate. One mL and 0.1 mL of the neutralized samples were pour plated in quadruplicate using Plate Count Agar.

This experiment determined the ability of the disinfectant to inactivate at least $10^6$ cfu/m of *Staphylococcus aureus*. The results of these measurements are shown above. All of the disinfectants were effective against the *Staphylococcus aureus* with the exception of 10% PVP-$I_2$ at a 1/1,000 dilution. The peroxidase based iodine germicide exhibited a 6 log reduction of *Staphylococcus aureus* within 30 seconds at free molecular iodine levels of 63 and 114 ppm; at a free molecular iodine level of 13 ppm the peroxidase based iodine germicide required 5 minutes to effect a 6 log inactivation of *Staphylococcus aureus*.

Microscopic examination of the RBCs treated with the peroxidase based iodine germicide RBC showed no morphologic changes or reduction in counts of the cells. The RBCs treated with 10% PVP-$I_2$ appeared discolored and shriveled with no reduction in count except for the 10% PVP-$I_2$ sample that was diluted 1/1000. The level of free molecular iodine in the 1/1000 dilution of 10% PVP-$I_2$ was determined to be 6 ppm.

| Inactivation of *Staphylococcus aureus* in the Presence of Red Blood Cells | | | | | | | |
|---|---|---|---|---|---|---|---|
| | Dilution of 10% PVP-$I_2$ | | | | Peroxidase Germicide Free Iodine Level | | |
| Timepoint | 1:20 | 1:100 | 1:200 | 1:1,000 | 10 | 63 | 114 |
| 30 seconds | pass | pass | fail | fail | fail | pass | pass |
| 60 seconds | | | pass | fail | fail | | |
| 120 seconds | | | | fail | fail | | |
| 300 seconds | | | | fail | pass | | |

EXAMPLE 4

An enzyme based iodine germicide was generated and its ability to inactivate viruses in the presence of a high concentration of red blood cells in human serum was determined. The germicide was made by dissolving 450 mg of sodium iodide in one liter of 0.05 molar citrate buffer at pH 5.5 and then simultaneously dissolving 10 mg of horseradish peroxidase (Sigma No. P8125). This solution was allowed to incubate for 10 minutes and then the virucidal efficacy of this formulation was determined.

Whole blood was processed by the Ficoll lymphocyte isolation procedure. The red blood cells (RBC) were recovered and washed once with phosphate buffered saline and held at a concentration of $6.5 \times 10^9$ RBC/mL in Alsevers solution at 5° C.

The tissue culture infective dose 50 ($TCID_{50}$) is the concentration of virus particles that causes 50% of a series of cultures to be infected. About $10^7$ units of $TCID_{50}$ vesicular stomatitis virus were added to samples of pooled human serum that contained $10^6$ RBCs per mL. This sample was incubated with the germicide for 5 minutes at 4° C. and at 25° C. After five minutes the virus titier was determined as follows. In quadruplicate, the sample was serially diluted fivefold in minimal essential media (MEM) nonessential amino acids solution containing 10% fetal calf serum and 0.1% sodium thiosulfate. The dilutions were plated onto 96-well plates containing Vero cells (ATCC CRL81) at approximately 80% confluency. The lowest dilution used in this assay was 1:5 of the original treated serum. The cultures were incubated for 3 days at 37° C. in a 5% $CO_2$ atmosphere and each well was examined for a cytopathic effect.

At both 4° and 25° C. no cytopathic effect was observed in mock infected and iodine-treated tissue culture wells. This indicates that the germicide was effective in inactivating a lipid enveloped virus in the presence of sensitive biological material. The effect that these formulations had on the cellular morphology of the red blood cells was determined by microscopic examination. Microscopic examination of the red blood cells indicated that the peroxidase based iodine germicide did not cause a morphologic change or reduce the number of RBCs. None of the treated cells appeared discolored or shriveled.

EXAMPLE 5

Suspension cells (CEM Lymphoblastic leukemia cells ATCC CCL-21) were grown in RPMI 1640 with 20% fetal bovine serum to plateau phase which equals approximately $2 \times 10^6$ cells per mL and then concentrated by centrifugation. These cells were then treated with free molecular iodine so that various ratios of free molecule iodine per cell were achieved (see Table 7a).

Attachment cells (Vero) were grown to confluency in T-75 flasks. The cells were removed by trpypsinization and then concentrated by centrifugation. These cells were then treated with free molecular iodine so that various ratios of free molecule iodine per cell were achieved (see Table 7b). The percent viability of the cells appears to be inversely proportional to the level of free molecular iodine per cell. An upper limit to the ratio of free molecular iodine per cell is apparent.

The data strongly suggests that it is feasible to expose sensitive biological materials to a concentration of free molecular iodine that is antibacterial but not cytotoxic.

TABLE 7a

Survival rate of CEM cells versus the number of iodine molecules per cell.

| Total Cells | ppm in 5 mls | Molecules molecular Iodine per cell | % viability | time after exposure |
|---|---|---|---|---|
| 1.00E + 09 | 5 | 5.94E + 09 | 96.4 | 18 hrs |
| 5.50E + 08 | 5 | 1.08E + 10 | 25.6 | 18 hrs |
| 5.50E + 08 | 5 | 1.08E + 10 | 31.8 | 18 hrs |
| 5.50E + 08 | 5 | 1.08E + 10 | 34.4 | 18 hrs |
| 5.20E + 08 | 5 | 1.14E + 10 | 18 | 18 hrs |
| 5.40E + 08 | 5 | 1.11E + 10 | 43.4 | 18 hrs. |
| 3.36E + 08 | 8 | 2.83E + 10 | 7.5 | (25 minutes) |
| 3.12E + 08 | 10 | 3.80E + 10 | 16.5 | (25 minutes) |
| 3.60E + 08 | 14 | 4.62E + 10 | 2.5 | (25 minutes) |
| 3.84E + 08 | 16 | 4.95E + 10 | 4.2 | (25 minutes) |
| 2.88E + 08 | 22 | 9.07E + 10 | 3.7 | (25 minutes) |

TABLE 7b

Vero Attachment Cells

| Total Cells | ppm in 5 mls | Molecules molecular Iodine | % viability | time measured |
|---|---|---|---|---|
| 1.90E + 08 | 5 | 3.12E + 10 | 59 | 40 min |
| 4.40E + 08 | 20 | 5.40E + 10 | 10.9 | |
| 1.10E + 08 | 5 | 5.40E + 10 | 61.1 | 20 min |
| 1.90E + 08 | 10 | 6.25E + 10 | 22 | 40 min |
| 2.10E + 08 | 13 | 7.35E + 10 | 24.3 | |
| 1.43E + 08 | 10 | 8.30E + 10 | 75 | estimate |
| 2.10E + 08 | 18 | 1.02E + 11 | 10.9 | |
| 1.81E + 07 | 5 | 3.28E + 11 | 0 | no recovery |
| 9.05E + 06 | 5 | 6.56E + 11 | 0 | no recovery |
| 4.50E + 06 | 5 | 1.32E + 12 | 0 | no recovery |
| 1.80E + 06 | 5 | 3.30E+ 12 | 0 | no recovery |

EXAMPLE 6

An enzyme based iodine germicide was generated and its ability to inactivate bacteria in the eyes of three month old male and female New Zealand white rabbits. The germicide was identical to the compositionn described as Treatment 1 in Example 1 except that enough sodium percarbonate was added to adjust the pH to 6.0 which lowered the level of free molecular iodine from 46 to 32 ppm.

Prior to test instillation of the germicide, all test and control eyes were judged free of significant ocular irritation. To detect or confirm any pre-existing corneal injury, the eyes were treated with fluorescein stain and observed in a darken room with ultraviolet light.

A small sample of the germicide (0.1 ml) was instilled into the lower conjunctival sac of the left eye of each rabbit and the lid held closed for one (1) second. The opposite eye of each rabbit remained untreated and served as the comparative control.

The eyes were examined for ocular reactions at one hour after test article instillation and again: at day 1, 2, 3, 4, 7, 14 and 21. The flourescein staining procedure was conducted at each time interval. One drop of fluorescein was administered by eye dropper to assess tissue damage. The results of these tests for days 1, 14 and 21 are shown below in Table 6.

No Corneal opacity nor iritis was observed in any of the animals during the test period. Minimal transient conjunctivitis was observed in 2/6 animals within 24 hours after treatment. This condition was abolished by day 2. No accessory orbital growth nor inflammation to the surrounding ocular structures was observed in any of the animals. The conclusion that was drawn was that the germicide did not cause irritation to the eye.

TABLE 6

| | | | Observation at Day Number | | |
|---|---|---|---|---|---|
| | 0 | 1 Hour | 1 | 14 | 21 |
| Corneal opacity | 0/6 | 0/6 | 0/6 | 0/6 | 0.6 |
| Iritis | 0/6 | 0/6 | 0/6 | 0/6 | 0/6 |
| Redness | 0/6 | 2/6 | 2/6 | 0/6 | 0/6 |
| Chemosis | 0/6 | 1/6 | 1/6 | 0/6 | 0/6 |
| Discharge | 0/6 | 1/6 | 1/6 | 0/6 | 0/6 |

A second experiment was conducted wherein 0.1 ml of a saline solution containing $10^6$ colony forming units of *Staphylococcus aureus* was instilled directly into the left eye of each of the rabbits used above. Five minutes was allowed to elapse and then the each eye was instilled with 0.1 ml of the germicide. The germicide was instilled every six hours for 24 hours and then the left eye from each rabbit was swabbed with cotton. The cotton was plated onto an agar plate and the agar plates were incubated at 37° C. for five days. No colonies of *Staphylococcus aureus* were observed on any of the rabbit eyes.

We claim:

1. A method for therapeutically treating a mammalian eye to disinfect said eye from pathogenic organisms comprising the steps of admixing a composition consisting essentially of a peroxidase selected from the Enzyme Commission No. E.C. 1.11.1.7, a source of hydrogen peroxide and an iodide source in a controlled molar ratio of hydrogen peroxide to iodide of between about 0.5 to 4.0 with an aqueous liquid medium in which the source of hydrogen peroxide after the formation of said mixture is controlled to provide a maximum concentration of hydrogen peroxide of 0.015% thereby forming a non-irritating microbiocide having a plurality of iodine species with at least 25% free molecular iodine on a molar basis and a controlled free molecular iodine concentration of between 5 and 125 ppm and applying said admixture to the eye.

2. A method as defined in claim 1 wherein said composition further comprises a buffer agent to maintain the pH of said liquid microbiocide at between pH 6.0 and 7.1.

3. A method as defined in claim 2 wherein said buffering agent is selected from the group consisting of glycine, phthalate acid, citric acid, phosphate, borate, barbituric acid, glutaric acid, dimethylglutarate, acetic acid, sodium acetate, succinic acid-sodium succinate, cacodylic acid, sodium hydrogen maleate, sodium bicarbonate, imidazole, TRIS (tris(hydroxymethyl)aminoethane), MES (2-[N-morpholino]ethanesulfonic acid), BIS-TRIS (bis[2-hydroxyethyl]imino-tris[hydroxymethyl]methane; 2-bis[2-hydroxyethyl]amino-2-[hydroxymethyl]-1,3-propanediol), ADA (N-[2-acetamido]-2-iminodiacetic acid; N-[carbamoylmethyl]iminodiacetic acid), ACES ((2-[(2-amino-2-oxoethyl)amino]ethanesulfonic acid; N-[2-acetamido]-2-aminoethane-sulfonic acid) and PIPES (piperazine-N, N'-bis[2-ethanesulfonic acid]; 1,4-piperazinediethanesulfonic acid).

\* \* \* \* \*